Figure 1:
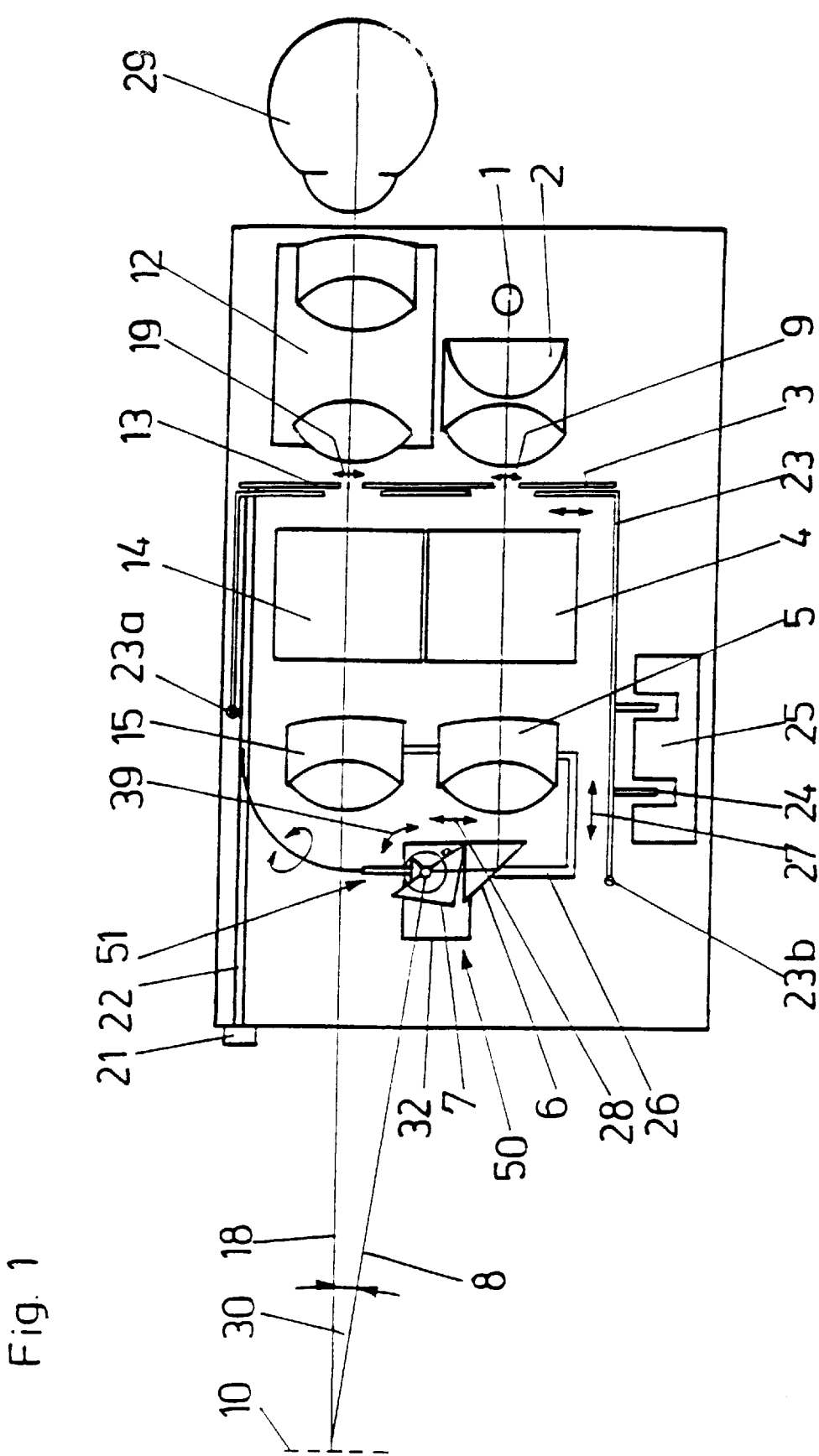

United States Patent [19]
Steinhuber

[11] Patent Number: 5,993,002
[45] Date of Patent: Nov. 30, 1999

[54] IMAGING OPTICAL INSTRUMENT

[76] Inventor: Wolfdietrich Steinhuber, Pertingerweg 10, A-6080 Igls, Austria

[21] Appl. No.: 09/043,104
[22] PCT Filed: Oct. 16, 1996
[86] PCT No.: PCT/AT96/00197
§ 371 Date: Jun. 18, 1998
§ 102(e) Date: Jun. 18, 1998
[87] PCT Pub. No.: WO97/15855
PCT Pub. Date: May 1, 1997

[30] Foreign Application Priority Data

Oct. 23, 1995 [DE] Germany .......................... 195 39 371

[51] Int. Cl.[6] ...................................................... A61B 3/10
[52] U.S. Cl. ............................................ 351/214; 359/214
[58] Field of Search ..................... 351/200, 205, 351/214; 359/212, 216, 220, 221, 223

[56] References Cited

U.S. PATENT DOCUMENTS 3,547,512  12/1970  Baer .
4,170,398  10/1979  Koester .

FOREIGN PATENT DOCUMENTS 0 608 516    9/1994   European Pat. Off. .
12 23 581 B  8/1966   Germany .
31 51 837    10/1982  Germany .
WO 83 02717  8/1983   Germany .
37 14 041    11/1988  Germany .

OTHER PUBLICATIONS

Scanning, vol. 12, XP000255795; Burns D.H. et al.: Scanning Slit Aperature Confocal Microscopy for Three-Dimensional Imaging.

Primary Examiner—George Manuel
Attorney, Agent, or Firm—Lorusso & Loud

[57] ABSTRACT

An imaging optical instrument with an optical system establishing an observation beam, and illuminating device generating a lighting beam, a slot-like observation diaphragm moving in an intermediate image plane of the observation beam and a slot-like lighting diaphragm moving synchronously in an intermediate image plane of the lighting beam, in which the observation beam and the lighting beam meet obliquely on the object plane and the slot images of the observation diaphragm and the lighting diaphragm substantially coincide in the object plane.

15 Claims, 3 Drawing Sheets

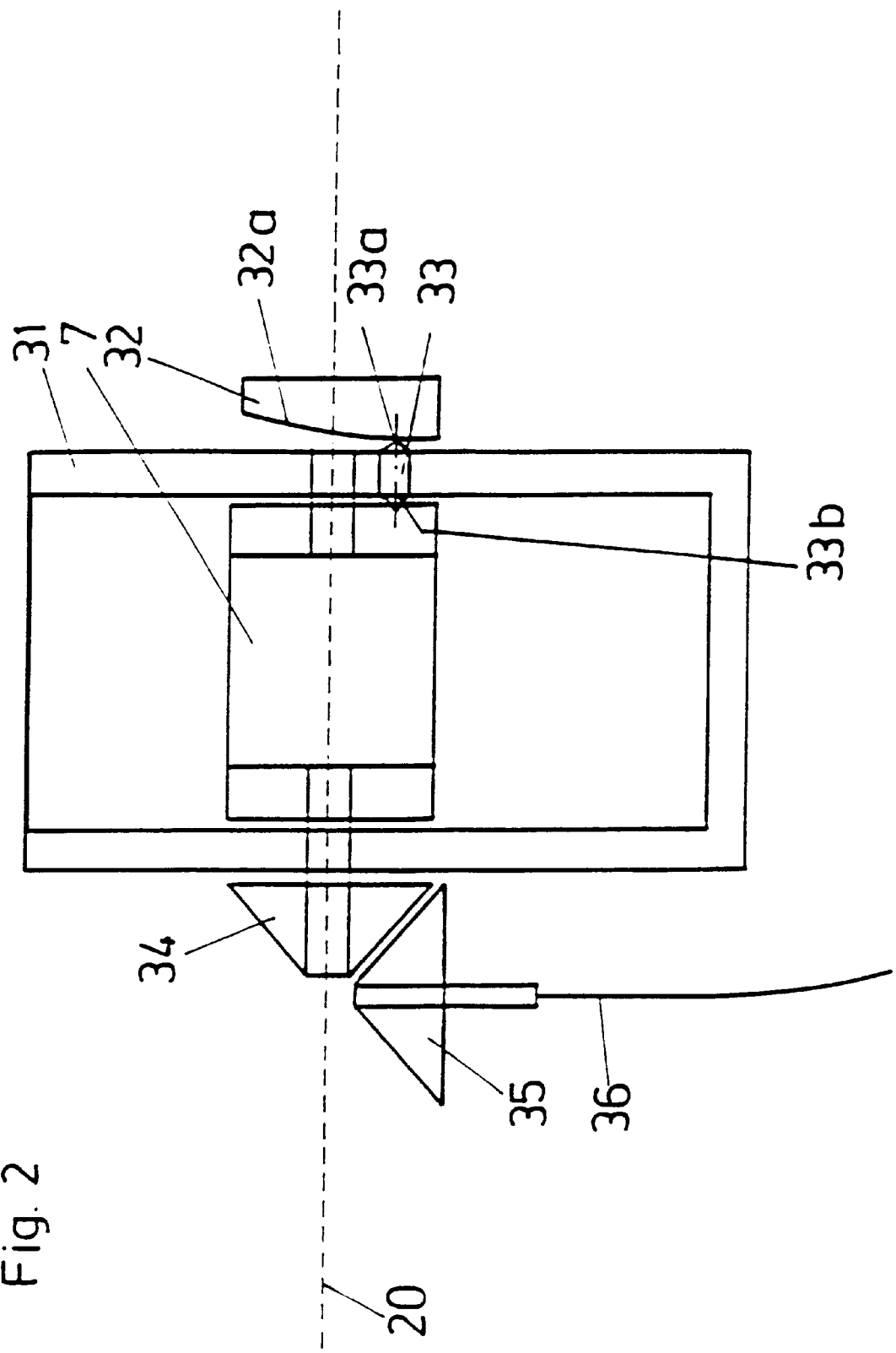

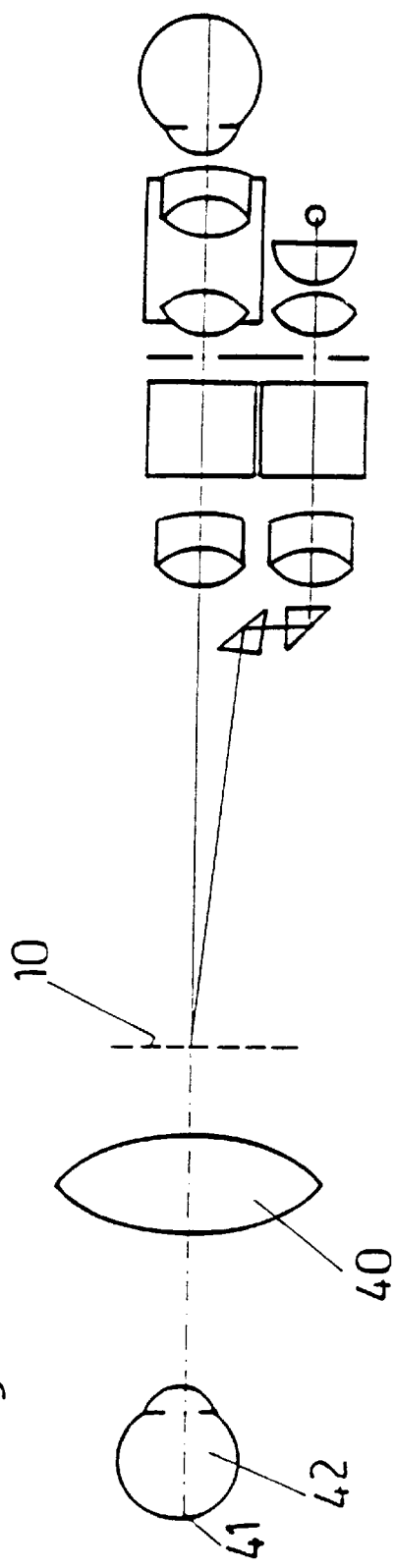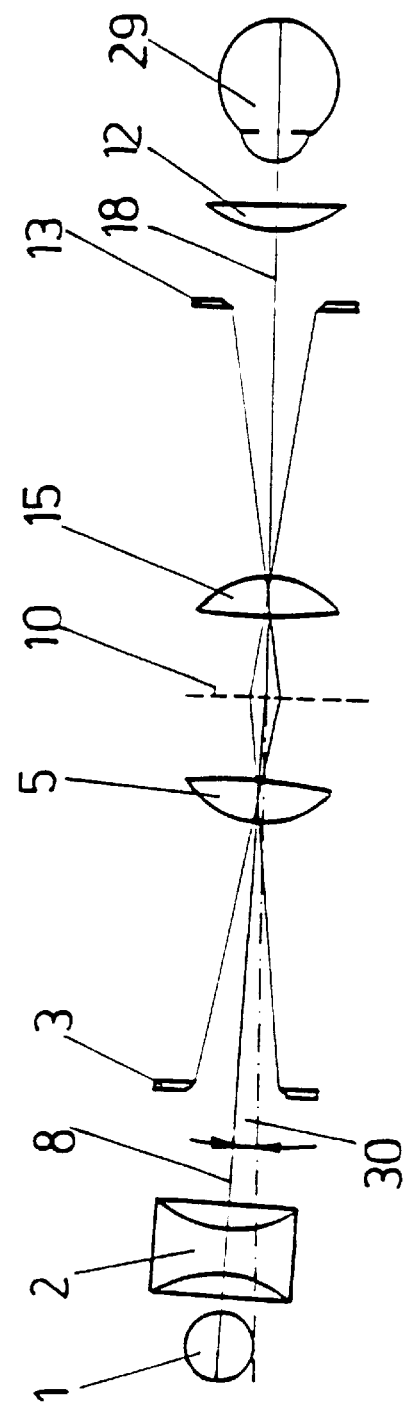

IMAGING OPTICAL INSTRUMENT

The invention relates to an imaging device for observation of an object in an object plane comprising an optical system establishing an observation beam and a lighting apparatus producing a lighting beam, the optical system comprising an observation diaphragm having a slit with a longitudinal extension, said observation diaphragm moving in an intermediate image plane of the observation beam, the lighting apparatus composing a lighting diaphragm having a slit with a longitudinal extension, said lighting diaphragm moving synchronously with said observation diaphragm and in an intermediate image plane of the lighting beam said slits of the observation diaphragm and of the lighting diaphragm producing slit images in said object plane, said slit images substantially coinciding in said object plane.

An apparatus of this type is known from U.S. Pat. No. 3,547,512. Only a small area of the object is lit and simultaneously observed through the slit-like diaphragms in the observation beam path and in the lighting beam path. In order to nevertheless be able to examine a larger part of the object, the lighting diaphragm and the observation diaphragm are moved synchronously, whereby a part of the object is scanned. If the object is observed using a detector which has a certain degree of inertia such as, for example, the human eye, and if the movement of the slit images of the diaphragms is rapid enough over the same part of the object repeatedly, the individual images then blend into a complete image of the scanned part of the object.

This process is intended in particular to improve the viewing of an object through a cloudy, that is to say opaque, medium, in that it reduces the production and the observation of scattered light and the glare resulting therefrom, and can therefore be used, for example, in indirect ophthalmoscopy for observing the retina of the eye. In this case, a true intermediate image of the retina is produced outside the eye by means of an ophthalmoscopy lens, wherein the lighting apparatus and the optical enlarging system are focused on the plane of this intermediate image.

Nevertheless, a satisfactory result still cannot be obtained using the measures previously described. In U.S. Pat. No. 3,547,512 additional diaphragms and mirrors are therefore used, which each mask half of the observation and lighting beams respectively so that the observation beam and the lighting beam travel separately from one another except in a small section in the object plane. Although the scattered light produced and observed is successfully further reduced in this way, nevertheless, because of the reduction in the apertures of the observation beam and of the lighting beam, the light intensity and the resolution obtainable are considerably reduced. Similar apparatuses with the same disadvantages are also known from U.S. Pat. No. 4,170,398 and EP-A2 197 781.

Another method for reducing glare is the dark-ground process, in which the lighting beam is not imaged in the lens when no object is present. Observable light results only from diffraction on the object, wherein, however, a faithful image is not produced, so this process is only used for representation of contours.

The object of the invention is to provide a novel optical enlarging or reducing device which improves the known apparatus and produces an image of the object even when observed through cloudy media, which is as well contrasted and free of glare as possible, such that the finest details become visible. The light intensity of the device and the resolution obtainable should also be as great as possible.

Very generally, using an optical imaging instrument, the beams of light emanating from an illuminated object are imaged through a lens as an intermediate image, and this is viewed, enlarged, through an eye piece. According to Abbe, the illumination light beams are diffracted (modulated) by the object, wherein diffractions of the zero order, first order and so forth occur and interfere. The beams of high light intensity of the zero order (not diffracted) interfere with the beams of lower light intensity of a higher order and make them more difficult to see, as only wavefronts of the same strength can produce a clear interference pattern.

An important advantage of the invention is therefore in that using the device according to the invention, although the non-diffracted zero order beams are reduced, they are not eliminated (as in the dark-ground process) so that by matching the amplitudes of diffracted and non-diffracted beams, the contrast can be significantly improved.

In a preferred embodiment of the invention, the angle of inclination between the observation beam and the lighting beam is adjustable. When the slit widths of the observation diaphragm and lighting diaphragm are kept constant, the contrast can be adjusted. On the other hand, it can be provided that the angle of inclination is coupled to the slit width, wherein a larger angle of inclination can be adjusted for a larger slit width in order to ensure a lack of glare with all slit widths and angles of inclination that can be set, and to keep the contrast constant.

Changing the direction of the lighting beam with respect to that of the observation beam is known in principle for an ophthalmoscope with a lighting apparatus, from DE-AS 12 23 581. This relates to an apparatus for direct ophthalmoscopy in which the retina is viewed by means of an observation beam incident parallel to the eye to be examined, without producing an intermediate image of the retina which is subsequently enlarged. The retina is therefore not scanned by means of synchronously moveable slit-shaped diaphragms, and the adjustment of the direction of the observation beam path serves not to increase contrast, but instead simply to allow the fields of vision of observation and lighting to coincide even in the case of eyes with defective vision.

Further advantages and details will be explained hereinafter with reference to the attached drawings.

In these is shown, in:

FIG. 1 a semi-schematic representation of a device according to the invention for reflected light microscopy, shown from the side, FIG. 2 a schematic detail drawing of a part of the lighting apparatus, viewed from the front, FIG. 3 the use of a device according to the invention in indirect ophthalmoscopy, FIG. 4 a device according to the invention configured as a transmitted light microscope.

The reflected light microscope shown in FIG. 1 is provided with a lighting apparatus, which comprises a light source 1, a condenser 2, a slit-shaped lighting diaphragm 3, a deviating prism 4, a lighting lens 5, a deviating prism 6 and a further deviating prism 7 defined as a lighting prism 7. A lighting beam 8, which is denoted in FIG. 1 by its central beam, is produced by the lighting apparatus. The optical system, composed of an eyepiece 12, slit-shaped observation diaphragm 13, deviating prism 14 and observation lens 15, establishes an observation beam with a central beam 18. The plane which is formed by the observation beam 18 and lighting beam 8 is therefore perpendicular to the longitudinal extent of the diaphragm slits 3, 13. The lighting diaphragm 3 and the observation diaphragm 13 are each arranged in intermediate image planes and their focused slit images should overlap as completely as possible in the object plane 10. The slit widths of the diaphragms 3, 13 are, as shown by the arrows 9, 19, adjustable by rotation of a knurled screw 21 with which a cam, which is not shown in FIG. 1, is actuated by means of a flexible shaft 22.

In order to move the diaphragms 3, 13 synchronously, and to thereby shift their slit images in the object plane 10 by substantially the same amount of displacement, whereby an object to be observed can be scanned, the diaphragms 3, 13 are arranged on an elastic supporting device 23, which is suspended in a rigid manner at its ends 23a, 23b. The supporting device is provided with plunger cores 24 which cooperate with an electromagnet 25 operated by alternating current or pulsed direct current to periodically displace the elastic supporting device 23. The effective length of the supporting device 23, and thereby its natural frequency, can be altered by means of the position of the suspension points 23a, 23b. The position of the suspension points 23a, 23b, the attachment site of the plunger cores 24, and the frequency of the alternating current are then coordinated such that a natural frequency of the supporting device 23 is excited resonantly by the electromagnets 25 so that a sufficiently large lateral displacement of the diaphragms 3, 13 is obtained. Naturally, the spring constant of the supporting device and its effective shock absorption are included. The size of the displacement of the diaphragms 3, 13 which determines the observed area of the object can inter alia be adjusted according to the degree of excitation and the amount of shock absorption. The frequency that causes oscillation of the supporting device 23 is selected such that the inertia of the detector, for example of the human eye 29, leads to blending of the individual images. For example, a frequency in the range of 50 Hz which is excited by the electromagnet 25 operated by alternating current from the public mains is suitable for this. The advantages of the drive apparatus described for the diaphragms 3, 13 are particularly in that the drive apparatus can be configured in a very compact manner and it causes only an extremely low level of noise.

The lenses 5, 15 and the prisms 6, 7 are both fitted to a supporting frame 26, shown schematically, which can be moved in the direction of the arrow 27 along the beam 8, 18 passing through the lenses 5, 15. In this way, the distance away of the object, that is to say the distance of the object plane 10 from the lenses 5, 15, and the enlargement and the aperture can be adjusted. In order to ensure that with any object distance set, the slit images of the lighting diaphragm 3 and of the observation diaphragm 13 coincide in the object plane 10, a control apparatus 50 is provided, which is further described hereinafter, which adjusts the angle of the lighting prism 7 and consequently the angle 30 between the lighting beam 8 and observation beam 18 depending on the distance away of the object. It is not usually troublesome that when there is an alteration in the angle 30 because of the alteration in the optical path of the lighting beam 8, the slit image of the lighting diaphragm 3 is no longer precisely focused in the object plane 10 of the observation beam 18. However, should this nevertheless be troublesome (particularly when there are relatively large angles 30), the Scheimpflug principle could be used. This states that the image of the lighting diaphragm 3 is focused in the object plane 10 when the object plane 10, the "effective object plane" and a plane containing the lighting diaphragm 3 intersect in one line. In the present case, as the lighting beam path 8 is bent by the deviating prisms 6, 7, "effective object plane" means a plane perpendicular to the direction of the lighting beam 8 incident on the object plane 10 and through the lens 5. The lighting diaphragm 3 could therefore be tilted in the object plane 10 according to the Scheimpflug principle for sharply focused imaging of the lighting slit.

Furthermore, the deviating prism 6 together with the lighting prism 7 can be moved in the direction of the arrow 28, that is to say in a direction perpendicular to the direction of the observation beam 18. The normal distance between the central beam of the observation beam 18 and the point of the observation prism 7 at which the central beam of the lighting beam 8 is deviated is hereinafter termed the base prism distance. The control apparatus 50 already described also adjusts the angle of the lighting prism 7 and consequently the angle 30 dependent upon the base prism distance such that for each adjustment of the base prism distance, the slit images of the observation diaphragm and of the lighting diaphragm substantially coincide in the object plane 10. With a constant slit width of the diaphragms 3, 13, the desired contrast of the image can be selected by means of the base prism distance. On the other hand, it can also be provided that the contrast is kept constant for different base prism distances and for different distances of the object in that a coupling apparatus 51 is provided for coupling the angle of the lighting prism 7 and thereby of the angle 30 to the slit widths of the diaphragms 3, 13.

The coupling apparatus 51 and the control apparatus 50 are explained hereinafter with reference to FIG. 1. As can be seen from FIG. 2, the lighting prism 7 is mounted rotatably on a frame 31. The control plate 32 can be seen in plan view in FIG. 1 and viewed from the side in FIG. 2. The control apparatus 50 for adjusting the angle of the prism 7 comprises a control plate 32, the surface of which is configured as a control surface 32a. A tip 33a of a control pin 33 lies against the control surface 32a. The other end 33b of the control pin 33, which also comes to a point, lies on a lateral surface of the prism 7 which is tensioned by a spring, which is not shown and is therefore pressed laterally against the control pin 33 acting as a wedge. When the supporting frame 26 is displaced in the direction of the arrow 27 or when the frame 31 is displaced relative to the supporting frame 26 in the direction of the arrow 28, the control pin 33 slides over the control surface 32a, appropriately curved in three dimensions, and is thereby displaced in a direction perpendicular to the lateral surface of the prism 7 against which it lies, and is influenced by the angle of the prism 7. The angle between the lighting beam 8 and the observation beam 18 to be set by means of the control surface 32a is thus dependent upon the base prism distance Z and upon the distance of the object O and equals INVTAN (Z/O). The distance of the object O depends, on the other hand, on the image width B which in FIG. 1 must always be the distance between the lens 5, 15 and the associated slit diaphragms B=(O.F)/(O-F), where F is the focal length of the lens 5, 15. For each position of the supporting frame 26 along the arrow 27, and for each position of the frame 31 along the arrow 28, the angle 30 is consequently known, and using known geometry of the wedge-shaped end 33b of the control pin 33 can be reproduced at a particular height of the control surface 32a.

The coupling apparatus 51 for coupling the angle of the prism 7 and the slit widths of the diaphragms 3, 13 can be provided with a bevelled wheel 34 connected to the prism 7, a bevelled wheel 35 meshing with said bevelled wheel and a flexible shaft 36 for transmission of the rotation of the bevelled wheel 35.

FIG. 3 shows an arrangement for using an apparatus according to the invention in indirect ophthalmoscopy. By means of an ophthalmoscope 40, the retina 41 of an eye 42 is imaged truly as an intermediate image in the object plane 10 of the apparatus according to the invention. With the apparatus according to the invention this intermediate image is enlarged with an adjustable enlargement, wherein by means of the inclined focal lighting together with the synchronously moved diaphragms, a high contrast observation of a corresponding part of the retina is possible. With increasing enlargement, the aperture also enlarges and thus the resolution. On the other hand the desired focal depth can be set by selection of the enlargement.

An embodiment of an apparatus according to the invention as a transmitted light microscope is shown in FIG. 4. The lighting beam 8 and the observation beam 18 are incident on the object plane 10 from different sides. Equivalent parts of the device are provided with the same reference numerals as in FIG. 1. The angle of inclination 30, which in this case is measured between the lighting beam 8 and the extension of the observation beam 18, is set according to the desired reduction of the zero diffraction light, whereby the contrast and lack of glare are increased. An alteration to the angle 30 can take place simply in the case of a transmitted light microscope configuration in that the lighting apparatus is arranged on a support, which is not shown in FIG. 4, which is pivotable about an axis perpendicular to the image plane and through the point of intersection of the object plane 10 with the observation beam 18 and the lighting beam 8. When the object distance is altered by adjusting the lens 15, no control apparatus for setting the angle 30 is necessary using this embodiment. However, a means for coupling the angle 30 and the gap widths of the diaphragms 3, 13 could be provided.

Instead of observation with the eye 29, a photographic or video camera coupled to the device can also be used. Laser light can be connected up for therapeutic purposes.

Instead of electromagnetic radiation in the visible range, electromagnetic radiation in another frequency range can be used, for example microwave radiation. The human eye naturally cannot be used for detection, but instead a sensor suitable for the radiation used. Furthermore, it is also conceivable and possible to use another type of radiation which has wave properties such as, for example, electron beams or acoustic waves.

I claim:

1. An optical imaging device for observation of an object in an object plane comprising an optical system establishing an observation beam and a lighting apparatus producing a lighting beam, wherein the observation beam and the lighting beam are incident on said object plane at an angle of inclination relative to one another which is different from zero and define a plane comprising said lighting beam and said observation beam, the optical system comprising an observation diaphragm having a sl it with a longitudinal extension, said observation diaphragm moving in an intermediate image plane of the observation beam, the lighting apparatus comprising an lighting diaphragm having a slit with a longitudinal extension, said lighting diaphragm moving synchronously with said observation diaphragm and in an intermediate image plane of the lighting beam, said slits of the observation diaphragm and of the lighting diaphragm producing slit images in said object plane, said slit images substantially coinciding in said object plane, said plane defined by said observation beam and said lighting beam being perpendicular to said longitudinal extensions of said slit images of the observation diaphragm and of the lighting diaphragm.

2. The optical device of claim 1, wherein said angle of inclination between said observation beam incident on said object plane and said lighting beam incident on said object plane is between 0.5 degrees and 30 degrees.

3. The optical device of claim 1, wherein said angle of inclination between said observation beam and said lighting beam is adjustable.

4. The optical device of claim 3, wherein in the case of configuration as a reflected light microscope, in said lighting beam a lighting prism is provided moveable in a direction of movement perpendicular to said observation beam and rotatable about an axis perpendicular to said plane which is defined by said observation beam and said lighting beam.

5. The optical device of claim 4, wherein a control apparatus is provided for rotating said lighting prism about said axis dependent upon the position of the lighting prism along said direction of movement such that said slit images of the observation diaphragm and of the lighting diaphragm substantially coincide in said object plane at all positions of the prism along said direction of movement.

6. The optical device of claim 3, wherein said slits of the observation diaphragm and of the lighting diaphragm have widths which are adjustable and wherein a coupling apparatus for coupling said angle of inclination between the observation beam and the lighting beam with said slit widths is present.

7. The optical device of claim 6, wherein said coupling apparatus couples said slit widths to an angle of rotation of said lighting prism about said axis.

8. The optical device of claim 1, wherein in the case of configuration as a transmitted light microscope, object distances of the observation beam and the lighting beam can be adjusted synchronously, wherein the angle of inclination between the observation beam and lighting beam are adjusted by means of a control apparatus such that the slit images of the observation diaphragm and of the lighting diaphragm always coincide in the object plane at the different object distances.

9. The optical device of claim 8, wherein the control apparatus adjusts the angle of inclination by rotation of the lighting prism.

10. The optical device of claim 5 or 8, wherein the control apparatus is provided with a curved control surface.

11. The optical device of claim 10, wherein the control apparatus is provided with a pin for rotating the lighting prism, one end of which pin is connected to the lighting prism, and the other end of which lies against the control surface, and is shifted when the lighting prism is moved along the control surface.

12. The optical device of claim 11, wherein the end of the control pin in contact with the lighting prism is configured as a wedge and lies against a lateral surface of the lighting prism which is pressed under tension against the control pin.

13. The optical device of claim 1, wherein deviating prisms are provided in the observation beam and in the lighting beam.

14. An drive apparatus for synchronous driving of an oscillatory movement of at least two optical diaphragms, wherein the diaphragms are arranged on an elastic supporting device or are configured as a part thereof, and wherein an electromagnet is provided for resonant excitation of oscillation of said supporting device.

15. The drive apparatus of claim 14, wherein a plunger core or a plunger coil is arranged on the supporting device.

* * * * *